(12) United States Patent
Hashimoto (10) Patent No.: US 12,205,710 B2
(45) Date of Patent: Jan. 21, 2025

(54) IMAGE GENERATION DEVICE, IMAGE GENERATION METHOD, IMAGE GENERATION PROGRAM, LEARNING DEVICE, LEARNING METHOD, AND LEARNING PROGRAM

(71) Applicant: FUJIFILM Corporation, Tokyo (JP)

(72) Inventor: Takayuki Hashimoto, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 151 days.

(21) Appl. No.: 18/058,875

(22) Filed: Nov. 28, 2022

(65) Prior Publication Data
US 2023/0089212 A1     Mar. 23, 2023

Related U.S. Application Data

(63) Continuation of application No. PCT/JP2021/014897, filed on Apr. 8, 2021.

(30) Foreign Application Priority Data

Jun. 4, 2020  (JP) .................. 2020-097900

(51) Int. Cl.
*G16H 30/40* (2018.01)
*G06N 3/0455* (2023.01)
(Continued)

(52) U.S. Cl.
CPC .......... *G16H 30/40* (2018.01); *G06N 3/0455* (2023.01); *G06N 3/0464* (2023.01); *G06N 3/08* (2013.01);
(Continued)

(58) Field of Classification Search
CPC ...... G16H 30/40; G16H 20/10; G06N 3/0455; G06N 3/0464; G06N 3/08; G06T 11/00; G06T 2210/41
See application file for complete search history.

(56) References Cited

U.S. PATENT DOCUMENTS 5,699,798 A * 12/1997 Hochman ............ A61B 5/0059
600/431
9,999,453 B2    6/2018 Overes
(Continued)

FOREIGN PATENT DOCUMENTS

| JP | 2014071592 | 4/2014 |
|---|---|---|
| JP | 2018525748 | 9/2018 |

(Continued)

OTHER PUBLICATIONS

Wibmer AG, Hricak H, Ulaner GA, Weber W. Trends in oncologic hybrid imaging. Eur J Hybrid Imaging. 2018;2(1):1. doi: 10.1186/s41824-017-0019-6. Epub Jan. 19, 2018. PMID: 29782605; PMCID: PMC5954767. (Year: 2018).*

(Continued)

*Primary Examiner* — Sun M Li (74) *Attorney, Agent, or Firm* — JCIPRNET (57) ABSTRACT

Provided are an image generation device, an image generation method, an image generation program, a learning device, a learning method, and a learning program that can check an efficacy of a medicine. A processor acquires a medical image including a lesion and information related to a type of medicine to be administered to a patient, from whom the medical image has been acquired, and an administration period of the medicine. The processor generates, from the medical image, a post-administration image indicating the lesion after the medicine is administered to the patient for the administration period.

19 Claims, 9 Drawing Sheets

(51) Int. Cl.
  *G06N 3/0464* (2023.01)
  *G06N 3/08* (2023.01)
  *G06T 11/00* (2006.01)
  *G16H 20/10* (2018.01)

(52) U.S. Cl.
  CPC ............. *G06T 11/00* (2013.01); *G16H 20/10* (2018.01); *G06T 2210/41* (2013.01)

(56) References Cited

U.S. PATENT DOCUMENTS

| | | | |
|---|---|---|---|
| 2014/0095202 A1 | 4/2014 | Kudou et al. | |
| 2015/0133784 A1* | 5/2015 | Kapoor | A61B 8/5246 600/438 |
| 2017/0076062 A1* | 3/2017 | Choi | G16C 20/30 |
| 2018/0330500 A1 | 11/2018 | Sakurai et al. | |
| 2019/0354882 A1* | 11/2019 | Sharma | G16H 30/20 |
| 2020/0227162 A1* | 7/2020 | Okumiya | G16H 40/20 |
| 2020/0410721 A1* | 12/2020 | Farri | G06F 40/279 |
| 2021/0174938 A1* | 6/2021 | Park | G16H 30/40 |
| 2021/0375401 A1 | 12/2021 | Choi et al. | |
| 2022/0215936 A1* | 7/2022 | Tachibana | G06F 17/12 |
| 2023/0029695 A1* | 2/2023 | Woo | G16H 20/10 |

FOREIGN PATENT DOCUMENTS

| | | |
|---|---|---|
| JP | 2018187384 | 11/2018 |
| JP | 2019093219 | 6/2019 |
| WO | 2019078259 | 4/2019 |

OTHER PUBLICATIONS

S. Mitra and B. U. Shankar, "Integrating Radio Imaging With Gene Expressions Toward a Personalized Management of Cancer," in IEEE Transactions on Human-Machine Systems, vol. 44, No. 5, pp. 664-677, Oct. 2014, doi: 10.1109/THMS.2014.2325744. (Year: 2014).*

S. Ravishankar, J. C. Ye and J. A. Fessler, "Image Reconstruction: From Sparsity to Data-Adaptive Methods and Machine Learning," in Proceedings of the IEEE, vol. 108, No. 1, pp. 86-109, Jan. 2020, doi: 10.1109/JPROC.2019.2936204. (Year: 2020).*

S. Mandal, A. B. Greenblatt and J. An, "Imaging Intelligence: AI Is Transforming Medical Imaging Across the Imaging Spectrum," in IEEE Pulse, vol. 9, No. 5, pp. 16-24, Sep.-Oct. 2018, doi: 10.1109/MPUL.2018.2857226. (Year: 2018).*

"Office Action of Japan Counterpart Application", issued on Oct. 3, 2023, with English translation thereof, p. 1-p. 4.

Yu-Chiao Chiu et al., "Predicting drug response of tumors from integrated genomic profiles by deep neural networks", International Conference on Intelligent Biology and Medicine (ICIBM 2018), May 2018, pp. 1-38.

Satoshi Kozawa et al., "Predicting Human Clinical Outcomes Using Mouse Multi-Organ Transcriptome", iScience, Feb. 2020, pp. 1-31.

Tomoki Uemura et al., "Use of generative adversarial network for survival prediction in patients with interstitial lung diseases", FIT2019 (The 18th Forum on Information Technology), submit with English translation, Dec. 2019, pp. 1-6.

"International Search Report (Form PCT/ISA/210) of PCT/JP2021/014897," mailed on Jun. 22, 2021, with English translation thereof, pp. 1-6.

"Written Opinion of the International Searching Authority (Form PCT/ISA/237) of PCT/JP2021/014897," mailed on Jun. 22, 2021, with English translation thereof, pp. 1-6.

* cited by examiner

IMAGE GENERATION DEVICE, IMAGE GENERATION METHOD, IMAGE GENERATION PROGRAM, LEARNING DEVICE, LEARNING METHOD, AND LEARNING PROGRAM

CROSS-REFERENCE TO RELATED APPLICATIONS

This application is a Continuation of PCT International Application No. PCT/JP2021/014897 filed on Apr. 8, 2021, which claims priority under 35 U.S.C § 119(a) to Japanese Patent Application No. 2020-097900 filed on Jun. 4, 2020. Each of the above application(s) is hereby expressly incorporated by reference, in its entirety, into the present application.

BACKGROUND

Technical Field

The present disclosure relates to an image generation device, an image generation method, an non-transitory computer recording medium storing an image generation program, a learning device, a learning method, and a non-transitory computer recording medium storing a learning program.

Related Art

In recent years, treatment centering on the administration of, for example, molecularly targeted medicines as anticancer agents has been performed for advanced cancers. A molecularly targeted medicine is a medicine that pinpoints and suppresses cell molecules causing aggravation of tumors to inhibit the aggravation. Molecularly targeted medicine has the advantages of high therapeutic efficacy and low side effects. The molecularly targeted medicine is administered according to a regimen which is a written treatment plan. The regimen includes, for example, the composition and amount of a solution in which a medicine is dissolved or diluted according to the characteristics of the medicine, the rate of administration, the order of administration, medicines used for countermeasures against side effects, and a withdrawal period after administration. The molecularly targeted medicine is administered according to the regimen, which makes it possible to provide effective treatment while preventing medical accidents. Meanwhile, the molecularly targeted medicine targets a specific molecule. Therefore, the efficacy of the molecularly targeted medicine differs depending on the type of cancer. In addition, in a case in which the medicine is continuously administered, the effect of the treatment weakens. Therefore, in some cases, it is better to switch the medicine to another molecularly targeted medicine. In addition, in a case in which there are a plurality of aggravating factors, it is necessary to establish a medicine administration plan and to effectively apply the plan.

Meanwhile, various methods for evaluating the efficacy of medicines using images have been proposed. For example, JP2018-525748A discloses a method for calculating data in a case in which a medicine is delivered, using a blood vessel anatomical model of a patient.

However, in the method disclosed in JP2018-525748A, it is not possible to check how much therapeutic effect is exhibited by the administration of the medicine. In addition, in particular, in a case in which the molecularly targeted medicine is used, it is not possible to check how long it takes for the medicine to become less effective.

SUMMARY OF THE INVENTION

The present disclosure has been made in view of the above circumstances, and an object of the present disclosure is to make it possible to check the efficacy of a medicine.

An image generation device according to the present disclosure comprises at least one processor. The processor is configured to acquire a medical image including a lesion and information related to a type of medicine to be administered to a patient, from whom the medical image has been acquired, and an administration period of the medicine, and generate, from the medical image, a post-administration image indicating the lesion after the medicine is administered to the patient for the administration period.

In addition, in the image generation device according to the present disclosure, the processor may be configured to generate the post-administration image using at least one learning model constructed by performing machine learning, for at least one type of medicine, using as training data, a combination of the administration period of the medicine to the patient, a first image before administration, and a second image after a lapse of the administration period.

Further, in the image generation device according to the present disclosure, the processor may be configured to acquire information related to a plurality of different administration periods and generate a plurality of post-administration images corresponding to the plurality of different administration periods, respectively.

Furthermore, in the image generation device according to the present disclosure, the processor may be further configured to derive information indicating an efficacy of the medicine corresponding to the administration period of the medicine on the basis of a change in the lesion between the plurality of post-administration images.

Moreover, in the image generation device according to the present disclosure, the processor may be configured to derive an administration stop time of the medicine on the basis of the efficacy of the medicine.

In addition, in the image generation device according to the present disclosure, the processor may be further configured to display at least one of the post-administration image, the information indicating the efficacy of the medicine, or the administration stop time on a display.

Further, in the image generation device according to the present disclosure, the processor may be configured to generate the plurality of post-administration images for each of a plurality of types of medicines.

Furthermore, in the image generation device according to the present disclosure, the processor may be further configured to derive information indicating an efficacy of the medicine corresponding to the administration period of the medicine on the basis of a change in the lesion between the plurality of post-administration images for each of the plurality of types of medicines.

Moreover, in the image generation device according to the present disclosure, the processor may be configured to derive an administration stop time of the medicine corresponding to a type of medicine to be administered, on the basis of the efficacy of the medicine.

In addition, in the image generation device according to the present disclosure, the processor may be further configured to display at least one of the plurality of post-administration images, the information indicating the efficacy of the medicine, the type of medicine to be administered, or the administration stop time on a display.

A learning device according to the present disclosure comprises at least one processor. The processor is configured to acquire, for at least one type of medicine, training data consisting of a combination of an administration period of the medicine to a patient, a first image before administration, and a second image after a lapse of the administration period, and perform training using the training data to construct a learning model that outputs a post-administration image indicating the lesion after the medicine is administered to the patient for the administration period in a case where a medical image of the patient including a lesion, a type of medicine, and the administration period are input.

An image generation method according to the present disclosure comprises: acquiring a medical image including a lesion and information related to a type of medicine to be administered to a patient, from whom the medical image has been acquired, and an administration period of the medicine; and generating, from the medical image, a post-administration image indicating the lesion after the medicine is administered to the patient for the administration period.

A learning method according to the present disclosure comprises: acquiring, for at least one type of medicine, training data consisting of a combination of an administration period of the medicine to a patient, a first image before administration, and a second image after a lapse of the administration period; and performing training using the training data to construct a learning model that outputs a post-administration image indicating the lesion after the medicine is administered to the patient for the administration period in a case where a medical image of the patient including a lesion, a type of medicine, and the administration period are input.

In addition, a non-transitory computer recording medium storing programs that cause a computer to perform the image generation method and the learning method according to the present disclosure may be provided.

According to the present disclosure, it is possible to check the efficacy of a medicine.

DETAILED DESCRIPTION

Figure 1:
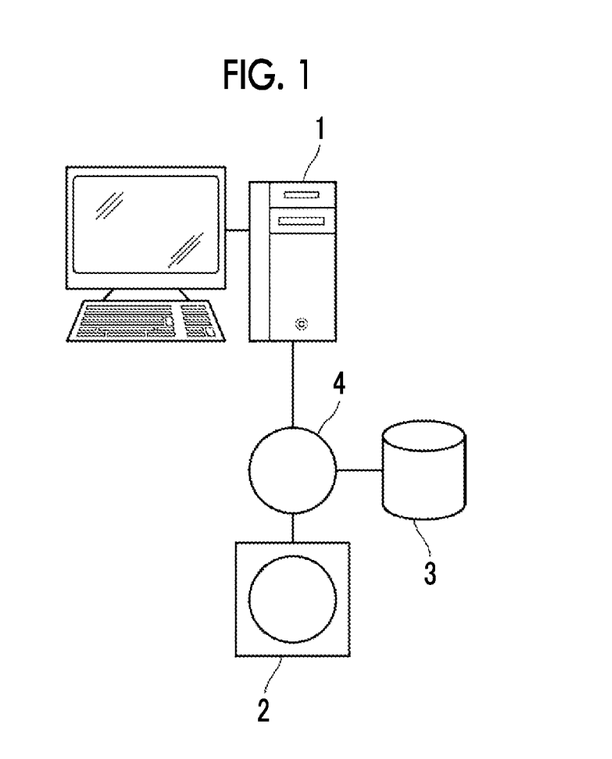
FIG. 1 is a diagram illustrating a schematic configuration of a medical information system to which an image generation device and a learning device according to an embodiment of the present disclosure are applied.

Hereinafter, an embodiment of the present disclosure will be described with reference to the drawings. First, a configuration of a medical information system to which an image generation device and a learning device according to this embodiment are applied will be described. FIG. 1 is a diagram illustrating a schematic configuration of the medical information system. In the medical information system illustrated in FIG. 1, a computer 1 including the image generation device and the learning device according to this embodiment, an imaging apparatus 2, and an image storage server 3 are connected through a network 4 such that they can communicate with each other.

The computer 1 includes the image generation device and the learning device according to this embodiment, and an image generation program and a learning program according to this embodiment are installed in the computer 1. The computer 1 may be a workstation or a personal computer that is directly operated by a doctor who performs diagnosis or may be a server computer that is connected to them through the network. In addition, the image generation program and the learning program are stored in a storage device of a server computer connected to the network or in a network storage in a state in which they can be accessed from the outside, and are downloaded and installed in the computer 1 used by the doctor upon request. Alternatively, the image generation program and the learning program are recorded on a recording medium, such as a digital versatile disc (DVD) or a compact disc read only memory (CD-ROM), are distributed, and are installed in the computer 1 from the recording medium.

The imaging apparatus 2 is an apparatus that images a diagnosis target part of a subject and that generates a three-dimensional image indicating the part and is specifically a computed tomography (CT) apparatus, a magnetic resonance imaging (MM) apparatus, a positron emission tomography (PET) apparatus, or the like. The three-dimensional image, which has been generated by the imaging apparatus 2 and consists of a plurality of slice images, is transmitted to the image storage server 3 and is then stored therein. In addition, in this embodiment, a diagnosis target part of a patient that is the subject is a lung, and the imaging apparatus 2 is a CT apparatus and generates a CT image of a chest including the lung of the subject as the three-dimensional image.

The image storage server 3 is a computer that stores and manages various types of data and that comprises a high-capacity external storage device and database management software. The image storage server 3 performs communication with other apparatuses through the wired or wireless network 4 to transmit and receive, for example, image data. Specifically, the image storage server 3 acquires various types of data including the image data of the three-dimensional image generated by the imaging apparatus 2 through the network, stores the acquired data in a recording medium, such as a high-capacity external storage device, and manages the data. In addition, the storage format of the image data and the communication between the apparatuses through the network 4 are based on a protocol such as Digital Imaging and Communication in Medicine (DICOM). Further, the image storage server 3 stores training data which will be described below.

Figure 2:
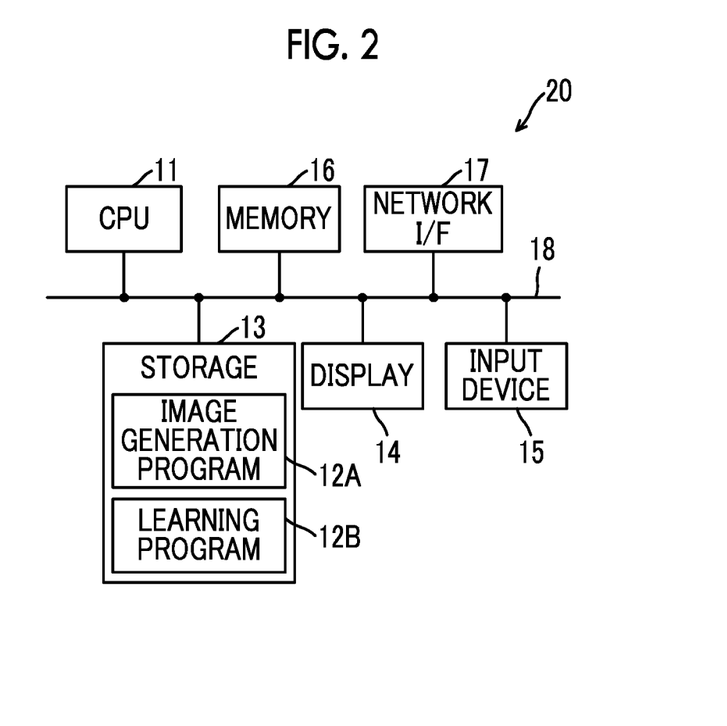
FIG. 2 is a diagram illustrating a schematic configuration of an image generation device and a learning device according to a first embodiment.

Next, an image generation device and a learning device according to a first embodiment will be described. FIG. 2 illustrates a hardware configuration of the image generation device and the learning device according to the first embodiment. As illustrated in FIG. 2, an image generation device and a learning device (hereinafter, in some cases, they are represented by an image generation device) 20 include a central processing unit (CPU) 11, a non-volatile storage 13, and a memory 16 as a temporary storage area. In addition, the image generation device 20 includes a display 14, such as a liquid crystal display, an input device 15, such as a keyboard and a mouse, and a network interface (I/F) 17 that is connected to the network 4. The CPU 11, the storage 13, the display 14, the input device 15, the memory 16, and the network I/F 17 are connected to a bus 18. In addition, the CPU 11 is an example of a processor according to the present disclosure.

The storage 13 is implemented by, for example, a hard disk drive (HDD), a solid state drive (SSD), or a flash memory. The storage 13 as a storage medium stores the image generation program and the learning program. The CPU 11 reads an image generation program 12A and a learning program 12B from the storage 13, develops the image generation program 12A and the learning program 12B in the memory 16, and executes the developed image generation program 12A and learning program 12B.

Figure 3:
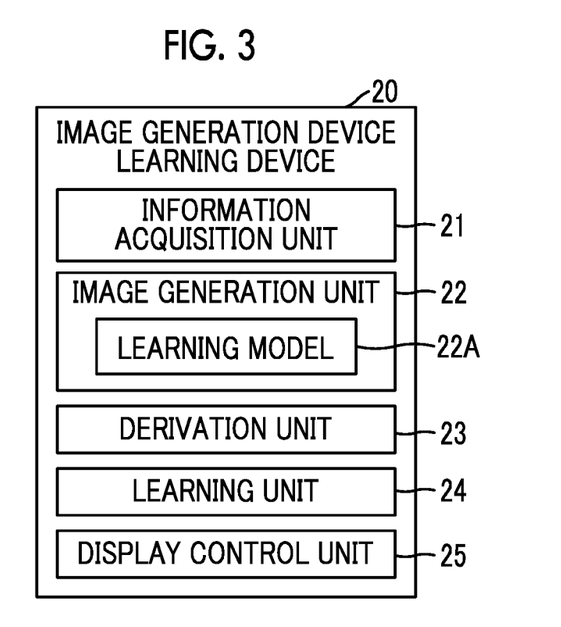
FIG. 3 is a functional configuration diagram illustrating the image generation device and the learning device according to the first embodiment.

Next, a functional configuration of the image generation device and of the learning device according to the first embodiment will be described. FIG. 3 is a diagram illustrating the functional configuration of the image generation device and of the learning device according to the first embodiment. As illustrated in FIG. 3, the image generation device 20 comprises an information acquisition unit 21, an image generation unit 22, a derivation unit 23, a learning unit 24, and a display control unit 25. The CPU 11 executes the image generation program 12A and the learning program 12B to function as the information acquisition unit 21, the image generation unit 22, the derivation unit 23, the learning unit 24, and the display control unit 25.

The information acquisition unit 21 acquires a medical image G0 including a lesion whose post-administration image, which will be described below, is to be generated from the image storage server 3 in response to an instruction from an operator through the input device 15. In addition, the information acquisition unit 21 acquires information, which is related to the type of medicine to be administered to the patient from whom the medical image G0 has been acquired and the administration period of the medicine, which have been input from the input device 15. Further, in this embodiment, it is assumed that information related to a plurality of different administration periods is acquired. Moreover, the information acquisition unit 21 acquires training data from the image storage server 3 in order to train a learning model 22A which will be described below.

The image generation unit 22 generates a post-administration image indicating a lesion after a medicine is administered to the patient for a certain administration period from the medical image G0. For this purpose, the image generation unit 22 has the learning model 22A that has been subjected to machine learning so as to output the post-administration image in a case in which the medical image G0, the type of medicine, and the administration period are input.

Figure 4:
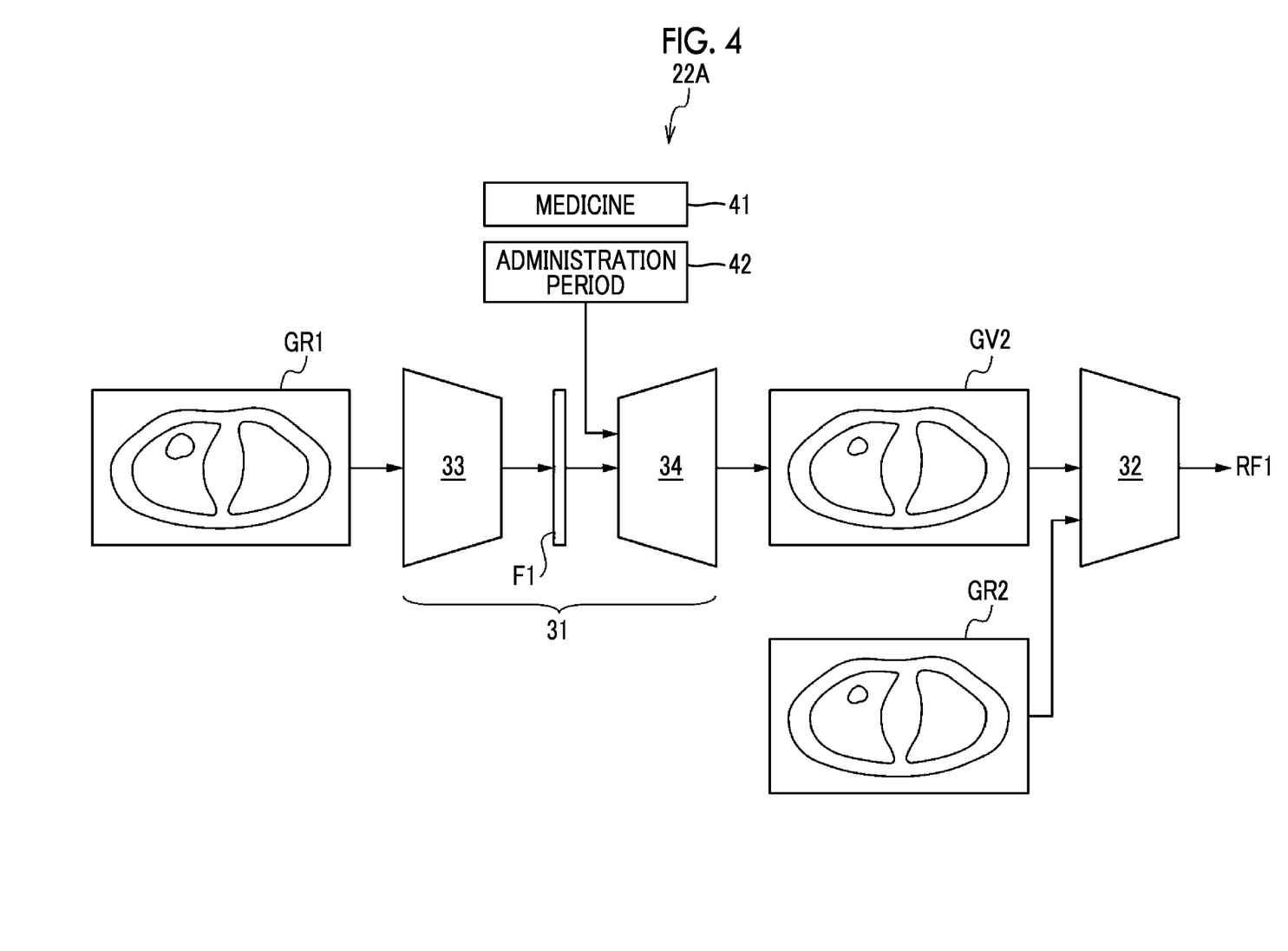
FIG. 4 is a schematic block diagram illustrating a configuration of a learning model in the first embodiment.

The learning model 22A is constructed by performing machine learning, for at least one type of medicine, using as training data, a combination of the administration period of the medicine to the patient, a first medical image before the administration, and a second medical image after a lapse of the administration period. For example, a generative adversarial network (GAN) can be used as the learning model 22A. FIG. 4 is a schematic block diagram illustrating a configuration of the learning model in this embodiment. In addition, in FIG. 4, the learning model 22A also includes elements used in a learning stage. As illustrated in FIG. 4, the learning model 22A has a generator 31 and a discriminator 32. The generator 31 has an encoder 33 and a decoder 34.

Figure 5:
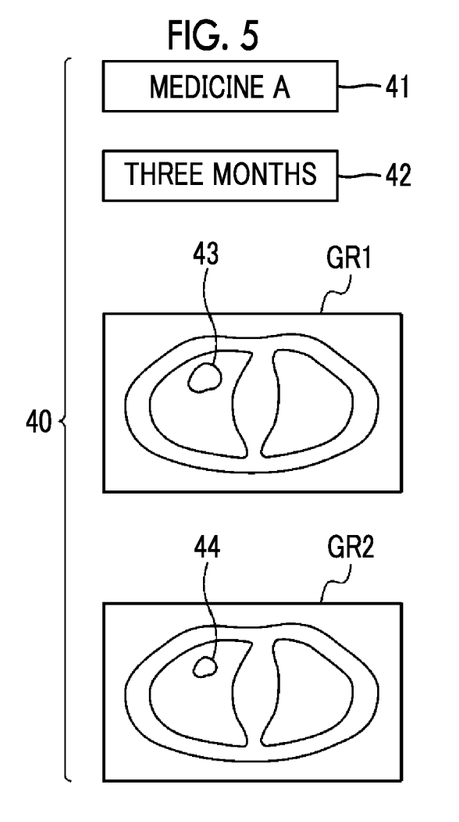
FIG. 5 is a diagram illustrating an example of training data used for learning.

FIG. 5 is a diagram illustrating an example of training data used for learning. As illustrated in FIG. 5, training data 40 consists of a label 41 of an administered medicine, a label 42 of an administration period of a medicine administered to a patient, a first medical image GR1 before administration, and a second medical image GR2 after the lapse of the administration period. As illustrated in FIG. 5, the label 41 of the medicine is, for example, a "medicine A". The label 42 of the administration period is, for example, 3 months. The first medical image GR1 is a tomographic image of the lung and has a lesion 43 appearing thereon. The second medical image GR2 is a tomographic image of the lung in the same cross section as that in the first medical image GR1 after the medicine A is administrated for three months to the same patient as that in the first medical image GR1. A lesion 44 included in the second medical image GR2 is smaller than the lesion 43 included in the first medical image GR1 due to the effect of the administration of the medicine. In addition, the lesion 44 included in the second medical image GR2 may be larger than the lesion 43 included in the first medical image GR1, depending on the administration period of the medicine or the efficacy of the medicine. Further, the density and/or shape of the lesion 44 may differ from the lesion 43 of the first medical image GR1 due to the effect of the administration of the medicine. Furthermore, in some cases, a plurality of types of medicines are combined in a case in which the medicines are administered. Therefore, the type of medicine is not limited to one type.

The encoder 33 consists of a convolutional neural network (CNN) which is one of multi-layered neural networks in which a plurality of processing layers are hierarchically connected and derives a feature map F1 indicating the feature amount of the input first medical image GR1.

The convolutional neural network consists of a plurality of convolutional layers. The convolutional layer performs a convolution process on the input image using various kernels and outputs a feature map consisting of feature amount data obtained by the convolution process. The kernel has a size of n×n pixels (for example, n=3), and a weight is set for each element. Specifically, a weight, such as a differential filter that enhances the edge of the input image, is set. The convolutional layer applies the kernel to the input image or to the entire feature map output from the processing layer in the previous stage while shifting a pixel of interest of the kernel. Further, the convolutional layer applies an activation function, such as a sigmoid function, to a convoluted value and outputs the feature map F1.

The decoder 34 derives a post-administration virtual medical image GV2 indicating the lesion after the medicine based on the label 41 is administered for the administration period based on the label 42 for the input first medical image GR1 on the basis of the feature map F1. That is, as illustrated in FIG. 4, in a case in which the feature map F1 of the first medical image GR1, the information related to the medicine based on the label 41, and the information related to the administration period based on the label 42 are input, the decoder 34 derives the post-administration medical image GV2 indicating the lesion after the medicine based on the label 41 is administered to the patient, from whom the first medical image GR1 has been acquired, for the administration period based on the label 42. In addition, the first medical image GR1 is an actual image acquired by imaging the patient with the imaging apparatus 2, that is, a real image. On the other hand, the medical image GV2 is a virtual image virtually generated from the first medical image GR1.

The decoder 34 has a plurality of deconvolutional layers. The deconvolutional layer performs the same process as the convolutional layer of the encoder 33 and applies a kernel for a deconvolution operation to the feature map while upsampling the input feature map F1. Specifically, as illustrated in FIG. 4, the decoder 34 performs a process of converting the lesion included in the first medical image GR1 into a lesion after the medicine based on the label 41 is administered for the administration period based on the label 42, while increasing the resolution of the feature map F1 output by the encoder 33 to the resolution of the first medical image GR1, to derive the medical image GV2 which is a post-administration virtual image.

The discriminator 32 consists of, for example, a convolutional neural network, determines the representation format of the input image and whether the input image is a real image or a virtual image generated by the decoder 34, and outputs a determination result RF1. The determination result indicates whether the input image is a real image or a virtual image.

Here, in a case in which the discriminator 32 determines that the input real image is a real image, the determination result RF1 is a correct answer. In a case in which the discriminator 32 determines that the input real image is a virtual image, the determination result RF1 is an incorrect answer. In addition, in a case in which the discriminator 32 determines that the input virtual image is a real image, the determination result RF1 is an incorrect answer. In a case in which the discriminator 32 determines that the input virtual image is a virtual image, the determination result RF1 is a correct answer. In this embodiment, in a case in which the medical image GV2 is input to the discriminator 32 during learning and the determination result RF1 is a virtual image, the determination result RF1 is a correct answer. In a case in which the determination result is a real image, the determination result is an incorrect answer. Further, in a case in which the second medical image GR2 which is a real image is input to the discriminator 32 during learning and the determination result RF1 is a real image, the determination result RF1 is a correct answer. In a case in which the determination result is a virtual image, the determination result is an incorrect answer.

The learning unit 24 derives a loss on the basis of the determination result RF1 output by the discriminator 32. In this embodiment, it is assumed that the loss in the discriminator 32 is a first loss L1.

Meanwhile, in this embodiment, it is desirable that the virtual medical image GV2 derived by the decoder 34 is completely matched with the second medical image GR2. Since the medical image GV2 has been processed by the encoder 33 and the decoder 34, there is a difference between the medical image GV2 and the second medical image GR2. In this embodiment, the learning unit 24 derives the difference between the medical image GV2 and the second medical image GR2 as a second loss L2.

In this embodiment, the learning unit 24 trains the discriminator 32 such that the determination result RF1 indicating whether the input image is a real image or a virtual image generated by the decoder 34 is a correct answer. That is, the learning unit 24 trains the discriminator 32 such that the first loss L1 is equal to or less than a predetermined threshold value.

In addition, the learning unit 24 trains the decoder 34 such that the medical image GV2 is matched with the second medical image GR2. Further, the learning unit 24 trains the encoder 33 so as to derive the feature map F1 that enables the decoder 34 to derive the medical image GV2 matched with the second medical image GR2. Specifically, the learning unit 24 trains the encoder 33 and the decoder 34 such that the second loss L2 is equal to or less than a predetermined threshold value.

In a case in which the training progresses, the encoder 33 and decoder 34 and the discriminator 32 increase their accuracy, and the discriminator 32 can accurately determine whether an input image is a real image or a virtual image no matter what expression format of an image is input. Meanwhile, the encoder 33 and the decoder 34 can generate a virtual image that is closer to the image of the real expression format and that is not determined by the discriminator 32. The generator 31 consisting of the encoder 33 and the decoder 34 which have been completely trained constitutes the learning model 22A according to this embodiment.

In addition, the learning unit 24 may perform machine learning using training data for various administration periods of each type of medicine assumed to be used to construct a plurality of learning models 22A corresponding to the types of medicines. Further, one learning model 22A may be constructed for a plurality of types of medicines, and post-administration images for the plurality of types of medicines may be generated by only one learning model 22A. Furthermore, not only one type of medicine but also a combination of a plurality of types of medicines may be used at once. For example, a medicine C and a medicine D may be administered at the same time. In this case, training data in a case in which the medicine C+D is administered is prepared, and the learning model 22A is constructed to generate a post-administration image in a case in which the medicine C+D is administered.

Figure 6:
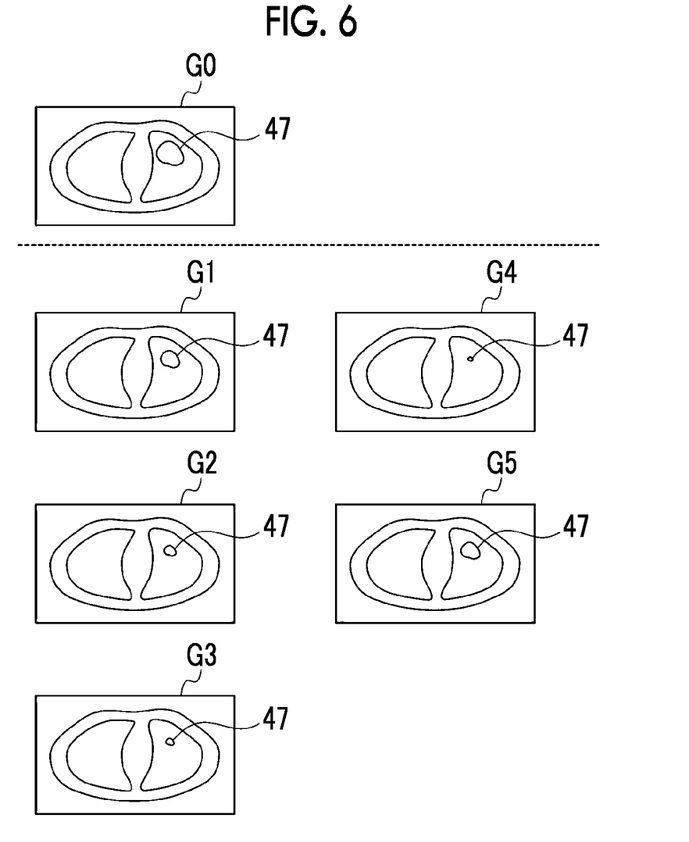
FIG. 6 is a diagram illustrating a medical image and a post-administration image.

The image generation unit 22 generates a post-administration image indicating a lesion after a certain medicine is administered to a patient for a certain administration period from the medical image G0, using the learning model 22A constructed as described above. The type of medicine and the administration period of the medicine are input by the operator through the input device 15 and are acquired by the information acquisition unit 21. In this embodiment, a plurality of post-administration images G1 to Gn are generated in a case in which a certain medicine is administered for a plurality of different administration periods. For example, as illustrated in FIG. 6, in a case in which information related to five administration periods of 10 days, 20 days, 30 days, 40 days, and 50 days is acquired for the acquired medical image G0, five post-administration images G1 to G5 for the administration periods of 10 days, 20 days, 30 days, 40 days, and 50 days are generated. As illustrated in FIG. 6, the size of a lesion 47 included in the medical image G0 is different in the post-administration images G1 to G5. That is, in the post-administration images G1 to G4, the size of the lesion 47 is smaller than that in the medical image G0 due to the lapse of the administration period. On the other hand, the size of the lesion 47 included in the post-administration image G5 is larger than the size of the lesion 47 included in the post-administration image G4 even though the medicine is administered. This shows that, after the lapse of an administration period of 40 days for a certain medicine, the efficacy of the medicine deteriorates and the lesion worsens.

Figure 7:
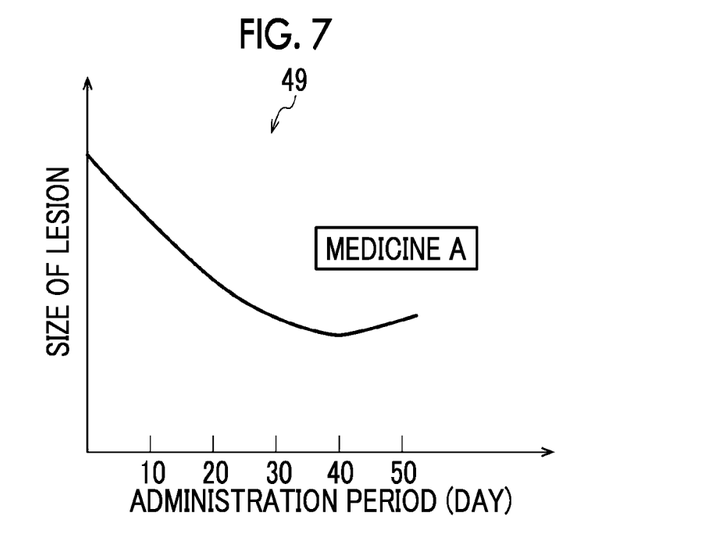
FIG. 7 is a diagram illustrating information indicating the efficacy of a medicine in the first embodiment.

The derivation unit 23 derives information indicating the efficacy of the medicine corresponding to the administration period of the medicine on the basis of a change in the size of the lesion for the plurality of post-administration images G1 to Gn. For this purpose, the derivation unit 23 detects the lesion 47 from the medical image G0 and from the plurality of post-administration images G1 to G5 and measures the size of the lesion 47. Then, the derivation unit 23 derives the relationship between the administration period and the size of the lesion as the information indicating the efficacy of the medicine corresponding to the administration period of the medicine. FIG. 7 is a diagram illustrating an example of the information indicating the efficacy of the medicine in the first embodiment.

As illustrated in FIG. 7, information 49 indicating the efficacy of the medicine is a graph in which a horizontal axis indicates the administration period and a vertical axis indicates the size of the lesion. In addition, in the information 49 indicating the efficacy of the medicine illustrated in FIG. 7, the size of the lesion between the administration periods of 10 days, 20 days, 30 days, 40 days, and 50 days may be derived by interpolating the size of the lesion for the administration periods of 10 days, 20 days, 30 days, 40 days, and 50 days. As illustrated in FIG. 7, in the information 49, the size of the lesion decreases until the administration period of 40 days. The size of the lesion increases after 40 days. Therefore, the derivation unit 23 derives a minimum value in the information 49 and derives the derived minimum value as the administration stop time of the medicine. In this embodiment, 40 days is derived as the administration stop time.

Figure 8:
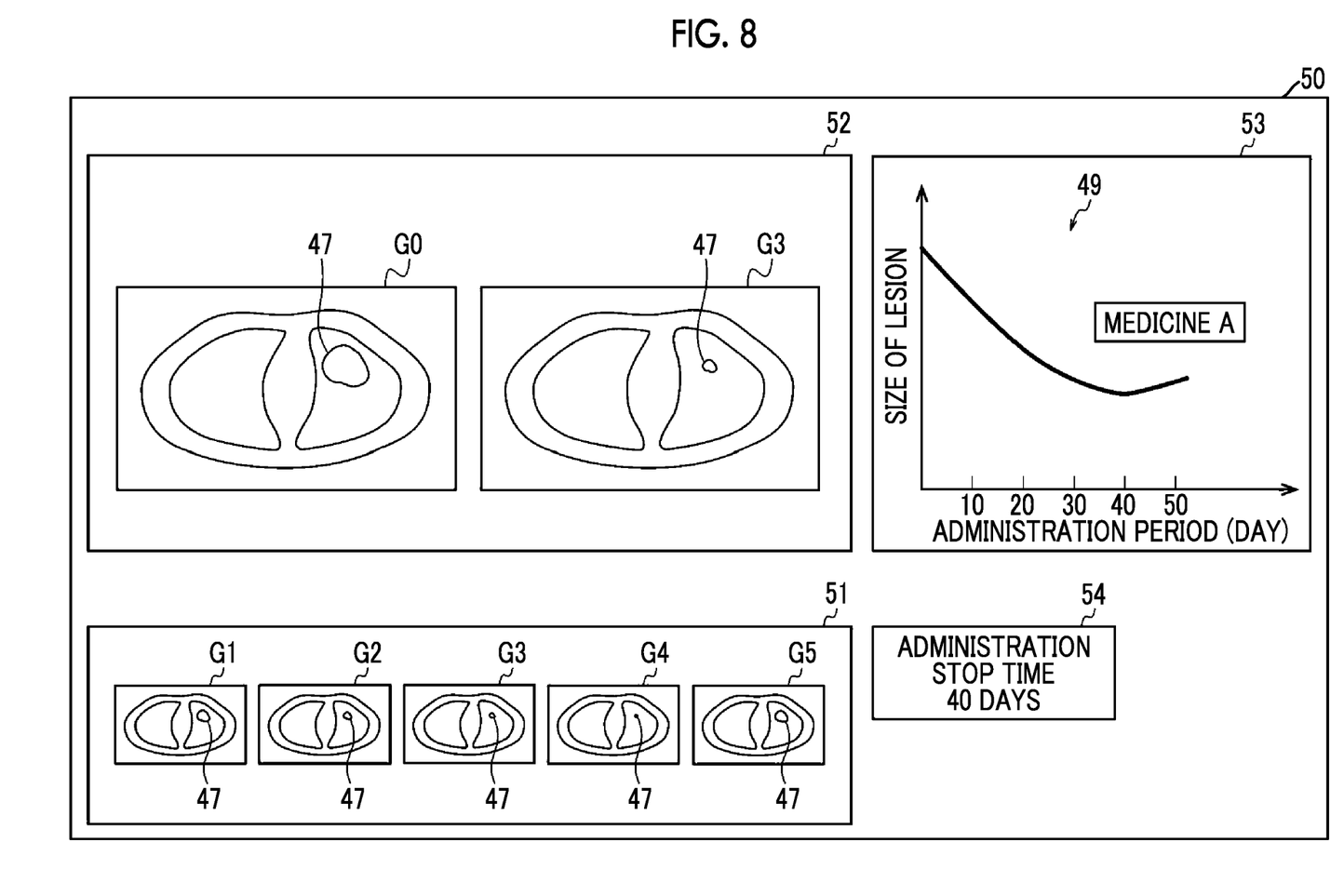
FIG. 8 is a diagram illustrating a display screen in the first embodiment.

The display control unit 25 displays the post-administration image, the information indicating the efficacy of the medicine, and the administration stop time on the display 14. FIG. 8 is a diagram illustrating a display screen for the post-administration image, the information indicating the efficacy of the medicine, and the administration stop time in the first embodiment. As illustrated in FIG. 8, a display screen 50 has a first display region 51, a second display region 52, a third display region 53, and a fourth display region 54.

A list of thumbnail images of the post-administration images G1 to G5 generated by the image generation unit 22 is displayed in the first display region 51. The medical image G0 and a post-administration image (here, the post-administration image G3) selected from the thumbnail images of the post-administration images G1 to G5 displayed in the first display region 51 are displayed in the second display region 52. The information 49 indicating the efficacy of the medicine derived by the derivation unit 23 is displayed in the third display region 53. The administration stop time derived by the derivation unit 23 is displayed in the fourth display region 54.

Figure 9:
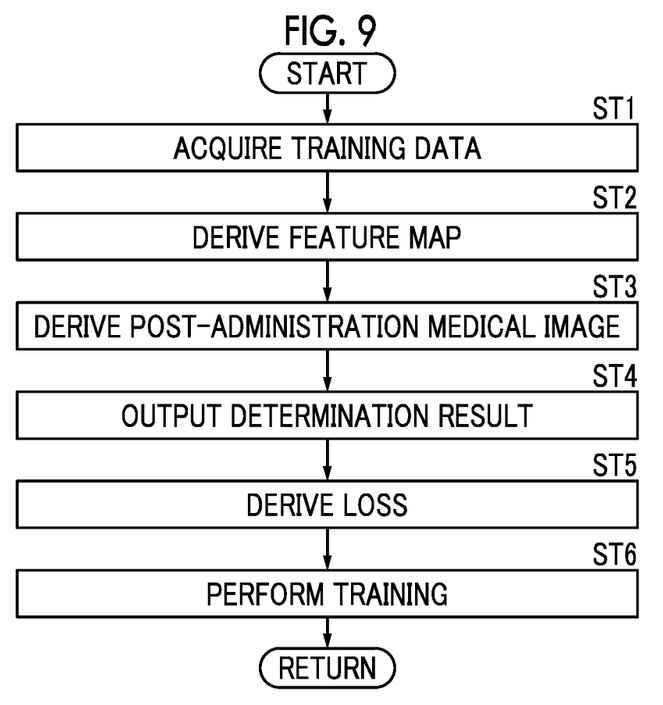
FIG. 9 is a flowchart illustrating a learning process performed in the first embodiment.

Next, a process performed in the first embodiment will be described. FIG. 9 is a flowchart illustrating a learning process performed in the first embodiment. In addition, it is assumed that training data used for learning is acquired from the image storage server 3 by the information acquisition unit 21 and is then stored in the storage 13. First, the learning unit 24 acquires the training data stored in the storage 13 (Step ST1). The learning unit 24 inputs the first medical image GR1 to the encoder 33 of the generator 31 such that the feature map F1 is derived (Step ST2). In addition, the learning unit 24 inputs the feature map F1, the information related to the medicine based on the label 41, and the information related to the administration period based on the label 42 to the decoder 34 such that the medical image GV2 after the lapse of the administration period is derived (Step ST3). Then, the learning unit 24 inputs the medical image GV2 after the lapse of the administration period to the discriminator 32 such that the determination result RF1 is output (Step ST4).

Then, the learning unit 24 derives the first loss L1 on the basis of the determination result RF1 and derives the difference between the medical image GV2 and the second medical image GR2 as the second loss L2 (loss derivation; Step ST5). Further, the learning unit 24 trains the encoder 33, the decoder 34, and the discriminator 32 on the basis of the first loss L1 and the second loss L2 (Step ST6). Then, the process returns to Step ST1 to acquire the next training data from the storage 13. Then, the processes in Steps ST1 to ST6 are repeated. In this way, the learning model 22A is constructed.

In addition, the learning unit 24 repeats the training until each of the first loss L1 and the second loss L2 is equal to or less than a predetermined threshold value. However, the learning unit 24 may repeat the training a predetermined number of times.

Figure 10:
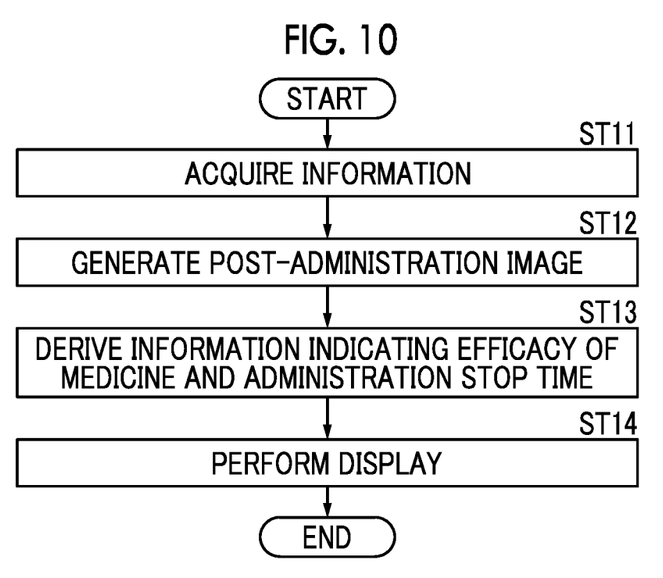
FIG. 10 is a flowchart illustrating an image generation process performed in the first embodiment.

Next, an image generation process performed in the first embodiment will be described. FIG. 10 is a flowchart illustrating the image generation process performed in the first embodiment. The information acquisition unit 21 acquires the target medical image G0 and information related to the type of medicine to be administered and the administration period (information acquisition; Step ST11). Then, the image generation unit 22 generates a post-administration image corresponding to the type of medicine to be administered and the administration period (Step ST12). Further, the derivation unit 23 derives information indicating the efficacy of the medicine and the administration stop time (Step ST13). Then, the display control unit 25 displays the post-administration image, the information indicating the efficacy of the medicine, and the administration stop time on the display 14 (Step ST14). Then, the process ends.

As described above, in the first embodiment, the post-administration images G1 to G5 indicating the lesion after the medicine is administered to the patient for the administration period are generated from the medical image G0. Therefore, it is possible to check the effect of the administration of the medicine administered to the patient.

In addition, since the information indicating the efficacy of the medicine is derived on the basis of the post-administration images G1 to G5, it is possible to easily check the efficacy of the medicine with reference to the derived information.

Further, since the administration stop time is derived on the basis of the information indicating the efficacy of the medicine, it is possible to easily determine the time when the administration of the medicine is stopped, and the medicine is switched to a different medicine.

Next, a second embodiment of the present disclosure will be described. In addition, a configuration of an image generation device according to the second embodiment is the same as the configuration of the image generation device according to the first embodiment illustrated in FIG. 3, and only the process to be performed is different. Therefore, the detailed description of the device will not be repeated here.

The second embodiment differs from the first embodiment in that post-administration images are derived for a plurality of types of medicines. In the second embodiment, the derivation unit 23 derives information indicating the efficacy of the medicine and the administration stop time for each type of medicine.

Figure 11:
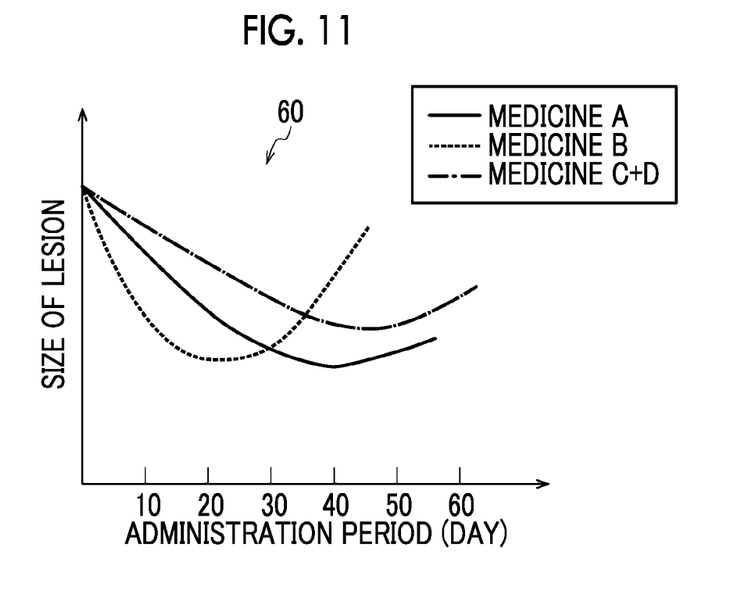
FIG. 11 is a diagram illustrating information indicating the efficacy of a medicine in a second embodiment.

FIG. 11 is a diagram illustrating an example of the information indicating the efficacy of the medicine in the second embodiment. As illustrated in FIG. 11, information 60 indicating the efficacy of the medicine in the second embodiment indicates a relationship between the administration period and the size of a lesion for the efficacy of three types of medicines of a medicine A, a medicine B, and a medicine C+D. In addition, the medicine C+D indicates that a medicine C and a medicine D are administered in combination. In FIG. 11, a solid line indicates the medicine A, a broken line indicates the medicine B, and a one-dot chain line indicates the efficacy of the medicine C+D. As illustrated in FIG. 11, for the medicine A, the size of the lesion decreases until an administration period of 40 days. After 40 days, the size of the lesion increases. For the medicine B, the size of the lesion decreases until an administration period of about 20 days. After 20 days, the size of the lesion increases. For the medicine C+D, the size of the lesion decreases until an administration period of about 50 days. After 50 days, the size of the lesion increases.

The derivation unit 23 derives a minimum value in the information 60 indicating the efficacy of each of the medicines A, B, and C+D and derives the derived minimum value as the administration stop time of the medicine. Specifically, 40 days for the medicine A, 20 days for the medicine B, and 50 days for the medicine C+D are derived as the administration stop time. Furthermore, in some cases, the derivation unit 23 derives, as the administration stop time of the medicine, a period when at least one of a rate of change of the size of lesion or a amount of change of the size of lesion is greater than threshold value instead of a period when the minimum value of the lesion was derived.

Figure 12:
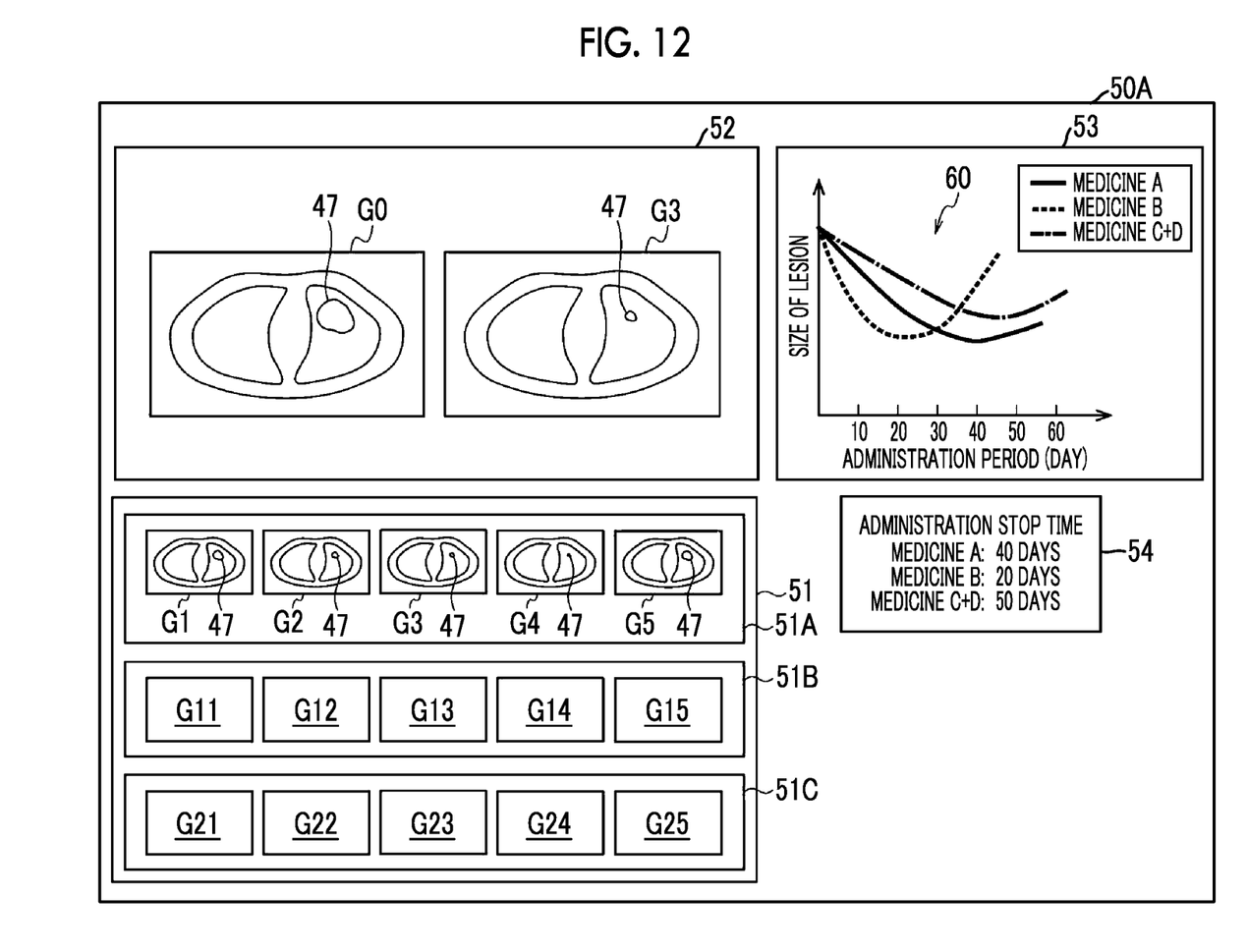
FIG. 12 is a diagram illustrating a display screen in the second embodiment.

FIG. 12 is a diagram illustrating a display screen for a post-administration image, the information indicating the efficacy of the medicine, and the administration stop time in the second embodiment. Further, in FIG. 12, the same configurations as those in FIG. 8 are denoted by the same reference numerals, and the detailed description thereof will not be repeated. As illustrated in FIG. 12, three display regions 51A to 51C are displayed in a first display region 51 of a display screen 50A in the second embodiment. Thumbnail images of post-administration images G1 to G5 generated for the medicine A are displayed in the display region 51A. Thumbnail images of post-administration images G11 to G15 generated for the medicine B are displayed in the display region 51B. Thumbnail images of post-administration images G21 to G25 generated for the medicine C+D are displayed in the display region 51C. In addition, in FIG. 12, the illustration of the content of the post-administration images G11 to G15 and G21 to G25 is omitted.

The medical image G0 and the post-administration images selected in the display regions 51A to 51C are displayed in the second display region 52.

Further, the information 60 indicating the efficacy of the medicine illustrated in FIG. 11 is displayed in the third display region 53. Information indicating the administration stop time of each of the medicines A, B, and C+D, for which the post-administration images have been generated, is displayed in the fourth display region 54. Specifically, 40 days for the medicine A, 20 days for the medicine B, and 50 days for the medicine C+D are displayed.

As described above, in the second embodiment, the post-administration images are generated for a plurality of types of medicines. Therefore, it is possible to check the efficacy of the medicines corresponding to the types of medicines.

In addition, since the information indicating the efficacy of the medicine corresponding to the type of medicine is derived, it is possible to easily check which medicine works better with reference to the derived information.

Further, since the administration stop time is derived on the basis of the information indicating the efficacy of the medicine, it is possible to easily determine the time when the administration of the medicine is stopped, and the medicine is switched to a different medicine for each type of medicine.

The post-administration image, the information indicating the efficacy of the medicine, and the administration stop time are displayed on the display screens 50 and 50A in each of the above-described embodiments. However, the present disclosure is not limited thereto. At least one of the post-administration image, the information indicating the efficacy of the medicine, or the administration stop time may be displayed.

Further, in each of the above-described embodiments, the learning model 22A is trained using an image including the entire lung as the training data. However, the present disclosure is not limited thereto. The learning model 22A may be trained using a partial image obtained by extracting only a lesion region from the image including the lung as the training data.

Furthermore, in each of the above-described embodiments, the technology of the present disclosure is applied to a case in which an interpretation report is made using a medical image, in which the lung is an object to be diagnosed, as a target image. However, the object to be diagnosed is not limited to the lung. In addition to the lung, any part of a human body, such as a heart, a liver, a brain, and limbs, can be used as the object to be diagnosed.

Moreover, in each of the above-described embodiments, for example, the following various processors can be used as a hardware structure of processing units performing various processes, such as the information acquisition unit 21, the image generation unit 22, the derivation unit 23, the learning unit 24, and the display control unit 25. The various processors include, for example, a CPU which is a general-purpose processor executing software (programs) to function as various processing units as described above, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or by a combination of two or more processors of the same type or different types (for example, a combination of a plurality of FPGAs or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As described above, various processing units are configured by one or more of the various processors as a hardware structure.

In addition, specifically, an electric circuit (circuitry) obtained by combining circuit elements, such as semiconductor elements, can be used as the hardware structure of the various processors.

What is claimed is:

1. An image generation device comprising at least one processor,
wherein the processor is configured to:
acquire and input a target medical image including a target lesion and information related to a target type of target medicine to be administered to a target patient, from whom the target medical image has been acquired, and a target administration period of the target medicine to a learned model constructed by performing machine learning, wherein the machine learning performed on the learned model comprising:
acquiring, for at least one type of medicine, training data consisting of a combination of an administration period of the medicine to a patient, a first image of the patient before administration, and a second image of the patent after a lapse of the administration period, wherein the first image and the second image are images generated by a medical imaging apparatus;
inputting the first image, information of the at least one type of medicine, information of the administration period of the medicine to the patient to a learning model;
deriving a training post-administration image indicating the lesion after the medicine is administered from the learning model; and
performing training using a difference between the second image and the training post-administration image to construct and update the learning model that outputs a post-administration image indicating the lesion after the medicine is administered to the patient for the administration period in a case where a medical image of the patient including a lesion, a type of medicine, and the administration period are input; and
generate a target post-administration image, outputted from the learned model, indicating the target lesion after the target medicine is administered to the target patient for the target administration period.

2. The image generation device according to claim 1, wherein the processor is configured to:
acquire information related to a plurality of different target administration periods; and
generate a plurality of target post-administration images corresponding to the plurality of different target administration periods, respectively.

3. The image generation device according to claim 2, wherein the processor is further configured to derive information indicating an efficacy of the target medicine corresponding to the target administration period of the target medicine on the basis of a change in the target lesion between the plurality of target post-administration images.

4. The image generation device according to claim 3, wherein the processor is further configured to derive information indicating a size of the target lesion in the target post-administration image for each of the plurality of different target administration periods, as information indicating the efficacy of the target medicine.

5. The image generation device according to claim 4, wherein the processor is further configured to interpolate the information indicating the size of the target lesion in the target post-administration image for each of the plurality of different target administration periods, as information indicating the efficacy of the target medicine, on the basis of the information indicating the size of the target lesion in the plurality of the target post-administration images corresponding to the plurality of different target administration periods.

6. The image generation device according to claim 4, wherein the processor is configured to derive a target administration stop time in which the size of the target lesion in the plurality of the target post-administration images has a smallest value.

7. The image generation device according to claim 3, wherein the processor is configured to derive a target administration stop time of the target medicine on the basis of the efficacy of the target medicine.

8. The image generation device according to claim 7, wherein the processor is further configured to display at least one of the target post-administration image, the information indicating the efficacy of the target medicine, or the target administration stop time on a display.

9. The image generation device according to claim 2, wherein the processor is configured to generate the plurality of target post-administration images for each of a plurality of target types of target medicines.

10. The image generation device according to claim 9, wherein the processor is further configured to derive information indicating an efficacy of the target medicine corresponding to the target administration period of the target medicine on the basis of a change in the target lesion between the plurality of target post-administration images for each of the plurality of target types of the target medicines.

11. The image generation device according to claim 10, wherein the processor is configured to derive a target administration stop time of the target medicine corresponding to the target type of the target medicine to be administered, on the basis of the efficacy of the target medicine.

12. The image generation device according to claim 11, wherein the processor is further configured to display at least one of the plurality of target post-administration images, the information indicating the efficacy of the target medicine, the target type of target medicine to be administered, or the target administration stop time on a display.

13. The image generation device according to claim 1, wherein the target medicine includes a set of medicines in which a plurality of types of medicines are combined, and
the processor is configured to:
acquire a type of medicine included in the set of medicines as the target type of the target medicine,
acquire information on an administration period of the set of medicines as the target administration period of the target medicine; and
generate, from the target medical image, the target post-administration image indicating the target lesion after the set of medicines is administered to the target patient for the target administration period.

14. The image generation device according to claim 1, wherein the machine learning performed on the learned model comprising:
  inputting the first image to the learning model;
  deriving a feature map of the first image from the learning model; and
  deriving the training post-administration image according to the feature map, information of the at least one type of medicine and information of the administration period of the medicine to the patient.

15. A learning device comprising at least one processor, wherein the processor is configured to:
  acquire, for at least one type of medicine, training data consisting of a combination of an administration period of the medicine to a patient, a first image of the patient before administration, and a second image of the patient after a lapse of the administration period, wherein the first image and the second image are images generated by a medical imaging apparatus;
  input the first image, information of the at least one type of the medicine, information of the administration period of the medicine to the patient to a learning model;
  derive a training post-administration image indicating the lesion after the medicine is administered from the learning model; and
  perform training using a difference between the second image and the training post-administration image to construct and update the learning model that outputs a post-administration image indicating the lesion after the medicine is administered to the patient for the administration period in a case where a medical image of the patient including a lesion, a type of medicine, and the administration period are input.

16. An image generation method comprising:
  acquiring and inputting a target medical image including a target lesion and information related to a target type of target medicine to be administered to a target patient, from whom the target medical image has been acquired, and a target administration period of the medicine to a learned model constructed by performing machine learning, wherein the machine learning performed on the learned model comprising:
    acquiring, for at least one type of medicine, training data consisting of a combination of an administration period of the medicine to a patient, a first image of the patient before administration, and a second image of the patent after a lapse of the administration period, wherein the first image and the second image are images generated by a medical imaging apparatus;
    inputting the first image, information of the at least one type of medicine, information of the administration period of the medicine to the patient to a learning model;
    deriving a training post-administration image indicating the lesion after the medicine is administered from the learning model; and
    performing training using a difference between the second image and the training post-administration image to construct and update the learning model that outputs a post-administration image indicating the lesion after the medicine is administered to the patient for the administration period in a case where a medical image of the patient including a lesion, a type of medicine, and the administration period are input; and
  generating a target post-administration image, outputted from the learned model, indicating the target lesion after the target medicine is administered to the target patient for the target administration period.

17. A learning method comprising:
  acquiring, for at least one type of medicine, training data consisting of a combination of an administration period of the medicine to a patient, a first image of the patient before administration, and a second image of the patient after a lapse of the administration period, wherein the first image and the second image are images generated by a medical imaging apparatus;
  inputting the first image, information of the at least one type of the medicine, information of the administration period of the medicine to the patient to a learning model;
  deriving a training post-administration image indicating the lesion after the medicine is administered from the learning model; and
  performing training using the training data a difference between the second image and the training post-administration image to construct and update the learning model that outputs a post-administration image indicating the lesion after the medicine is administered to the patient for the administration period in a case where a medical image of the patient including a lesion, a type of medicine, and the administration period are input.

18. A non-transitory computer recording medium storing an image generation program that causes a computer to execute:
  acquiring and inputting a target medical image including a target lesion and information related to a target type of target medicine to be administered to a target patient, from whom the target medical image has been acquired, and a target administration period of the medicine to a learned model constructed by performing machine learning, wherein the machine learning performed on the learned model comprising:
    acquiring, for at least one type of medicine, training data consisting of a combination of an administration period of the medicine to a patient, a first image of the patient before administration, and a second image of the patent after a lapse of the administration period, wherein the first image and the second image are images generated by a medical imaging apparatus;
    inputting the first image, information of the at least one type of medicine, information of the administration period of the medicine to the patient to a learning model;
    deriving a training post-administration image indicating the lesion after the medicine is administered from the learning model; and
    performing training using a difference between the second image and the training post-administration image to construct and update the learning model that outputs a post-administration image indicating the lesion after the medicine is administered to the patient for the administration period in a case where a medical image of the patient including a lesion, a type of medicine, and the administration period are input; and
  generating a target post-administration image, outputted from the learned model, indicating the target lesion after the target medicine is administered to the target patient for the target administration period.

19. A non-transitory computer recording medium storing a learning program that causes a computer to execute:
- acquiring, for at least one type of medicine, training data consisting of a combination of an administration period of the medicine to a patient, a first image of the patient before administration, and a second image of the patient after a lapse of the administration period, wherein the first image and the second image are images generated by a medical imaging apparatus;
- inputting the first image, information of the at least one type of the medicine, information of the administration period of the medicine to the patient to a learning model;
- deriving a training post-administration image indicating the lesion after the medicine is administered from the learning model; and
- performing training using a difference between the second image and the training post-administration image to construct and update the learning model that outputs a post-administration image indicating the lesion after the medicine is administered to the patient for the administration period in a case where a medical image of the patient including a lesion, a type of medicine, and the administration period are input.

* * * * *